United States Patent [19]

Kallok et al.

[11] Patent Number: 5,174,287
[45] Date of Patent: Dec. 29, 1992

[54] AIRWAY FEEDBACK MEASUREMENT SYSTEM RESPONSIVE TO DETECTED INSPIRATION AND OBSTRUCTIVE APNEA EVENT

[75] Inventors: Michael J. Kallok, New Brighton; H. Toby Markowitz, Roseville, both of Minn.

[73] Assignee: Medtronic, Inc., Minneapolis, Minn.

[21] Appl. No.: 706,165

[22] Filed: May 28, 1991

[51] Int. Cl.$^5$ ............................................. A61N 1/36
[52] U.S. Cl. ................................. 128/419; 128/721; 128/200.24
[58] Field of Search ................ 128/419 G, 419 R, 716, 128/721, 28, 200.24, 204.23, 733, 724, 421

[56] References Cited

U.S. PATENT DOCUMENTS

| | | | |
|---|---|---|---|
| 4,155,356 | 5/1979 | Venegas | 128/204.23 |
| 4,506,666 | 3/1985 | Durkan | 128/419 G |
| 4,570,631 | 2/1986 | Durkan | 128/419 G |
| 4,777,962 | 10/1988 | Watson et al. | 128/721 |
| 4,830,008 | 5/1989 | Meer | 128/421 |

FOREIGN PATENT DOCUMENTS 0404427 12/1990 European Pat. Off. .
8600234 1/1986 PCT Int'l Appl. ............. 128/419 G

OTHER PUBLICATIONS

Glenn, William W. L., Diaphragm Pacing: Present Status, 1977.
Cook, William R., & Osguthorpe, J. David, Obstructive Sleep Apnea: Diagnosis and Treatment, Dec. 1985.

Primary Examiner—Kyle L. Howell
Assistant Examiner—Kennedy J. Schaetzle
Attorney, Agent, or Firm—Harold R. Patton; Daniel W. Latham; John L. Rooney

[57] ABSTRACT

An improved apparatus for and method of providing feedback to an implantable pulse generator to treat obstructive sleep apnea. Sensors monitor the electrical activity associated with contractions of the diaphragm. The pressure within the thorax and the upper airway are also measured. Whenever electrical activity of the diaphragm suggests that an inspiration cycle is in progress and the pressure sensors show an abnormal pressure differential across the airway, the presence of obstructive sleep apenea is assumed and electrical stimulation is applied to the musculature of the upper airway.

5 Claims, 6 Drawing Sheets 5,174,287

AIRWAY FEEDBACK MEASUREMENT SYSTEM RESPONSIVE TO DETECTED INSPIRATION AND OBSTRUCTIVE APNEA EVENT

CROSS REFERENCE TO CO-PENDING APPLICATIONS

U.S. patent application Ser. No. 07/610,854, filed Nov. 8, 1990, now U.S. Pat. No. 5,133,354, entitled Muscle Tone: U.S. patent application Ser. No. 07/639,192, filed Jan. 9, 1991, entitled Servo Muscle Control; U.S. patent application Ser. No. 07/617,158, filed Nov. 23, 1990, entitled Multiple Stimulation Electrodes; and U.S. patent application Ser. No. 07/671,513, filed Mar. 19, 1991, entitled Demand Apnea Control are all assigned to the assignee of the present invention and incorporated herein by reference.

BACKGROUND OF THE INVENTION

1. Field of the Invention

The present invention relates generally to implantable medical devices, and more particularly relates to implantable medical devices for the treatment of obstructive sleep apnea.

2. Description of the Prior Art

The medical characteristics of sleep apnea have been known for some time. There are two generally recognized forms of the disease. The first is central sleep apnea which is associated with the failure of the body to automatically generated the neuro-muscular stimulation necessary to initiate and control a respiratory cycle at the proper time. Work associated with employing electrical stimulation to treat this condition is discussed in "Diaphragm Pacing: Present Status", by William W. L. Glenn, in *Pace,* Volume I, at pages 357-370 (July-September 1978).

The second condition is known as obstructive sleep apnea. It is discussed at some length in "Obstructive Sleep Apnea: Diagnosis and Treatment", by Drs. Cook and Osguthorpe in *Journal of South Carolina Medical Association,* 81 (12): 647-651 (December 1985).

At present, a tracheostomy may be the treatment of choice for a number of patients when obstructive sleep apnea is severe, although systems employing continuous positive air pressure (CPAP) are now available. However, some interest has been displayed in electrical stimulation of the muscle tissue along the upper airway during respiration. U.S. Pat. No. 4,830,008 issued to Meer discusses a technique for electrical stimulation of the muscles of the upper airway in synchrony with the respiratory cycle. U.S. Pat. No. 4,506,666 issued to Durkan discusses such stimulation in conjunction with pressurized airflow supplied by a respirator.

A key problem associated with electrical stimulation of the upper airway is detection of an apnea event. Some of the prior art systems apparently rely upon screening for employment of therapy. In these systems, the treatment is consistently applied without regard to a medical condition which might be intermittent. Yet other systems attempt to detect the onset of an apnea event using measurement of a parameter associated with apnea. The concern with such systems is in the accuracy of detection.

SUMMARY OF THE INVENTION

The present invention overcomes the problems found in the prior art by providing a system for the treatment of obstructive sleep apnea which employs a highly accurate detection technique. Detection is accomplished by measuring at least two different parameters.

The first parameter to be sensed is the electrical activity associated with contraction of the diaphragm. This may be measured using nerve or muscle electrodes. The signal is processed to derive an indication of when the patient is in the process of inspiration. Used alone, this measurement is deemed too noisy to provide accurate results without undesirable numbers of false positives.

Pressure sensors are used to monitor the pressure of the thorax and the upper airway. In this manner, the pressure difference can be correlated with the apparent contraction of the diaphragm to accurately determine when inspiration is in process and the airway is obstructed.

Upon detection of an apnea event, electrical stimulation is provided by an implantable pulse generator through an insulated lead to one or more electrodes to stimulate the muscles of the upper airway to remove the detected obstruction.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
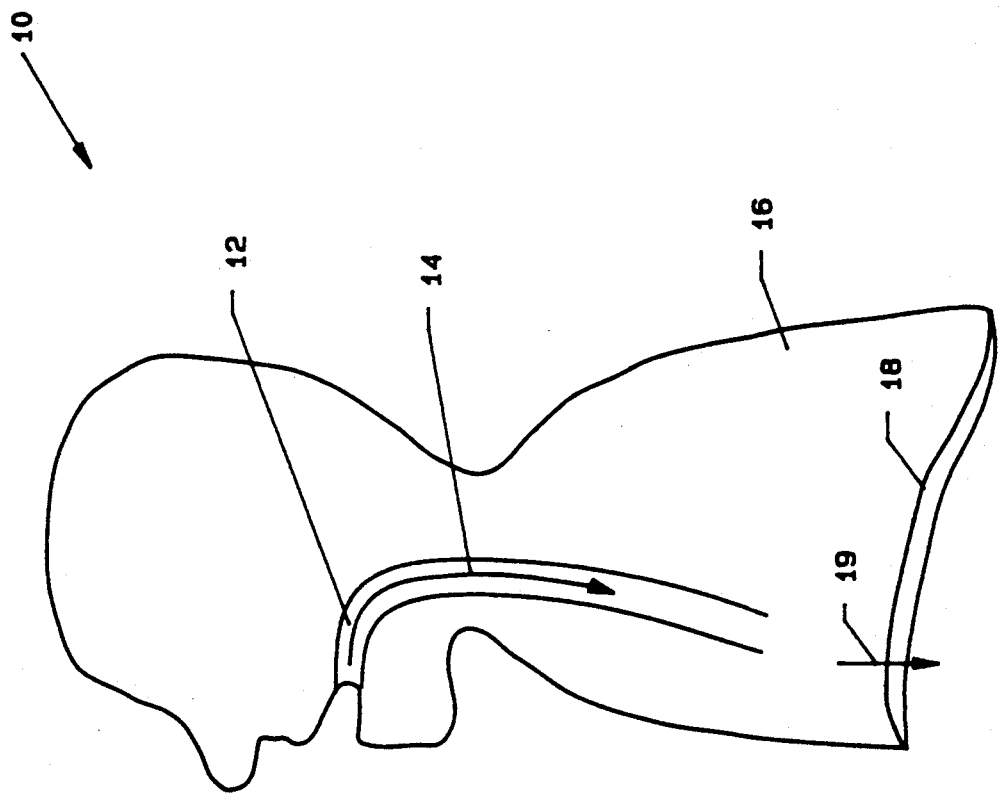
FIG. 1 is a schematic diagram of the respiratory system of a patient.

FIG. 1 is a schematic diagram of the respiratory system of patient 10 during inspiration. As a result, of muscular contraction, diaphragm 18 moves in the direction of arrow 19, which increases the volume of thorax 16. A partial vacuum is created causing air to enter upper airway 12 and proceed in the direction of arrow 14. This condition may be sensed by monitoring the EMG of diaphragm 18, pressure within thorax 16, airflow within upper airway 12, or other indication of inspiration.

Figure 2:
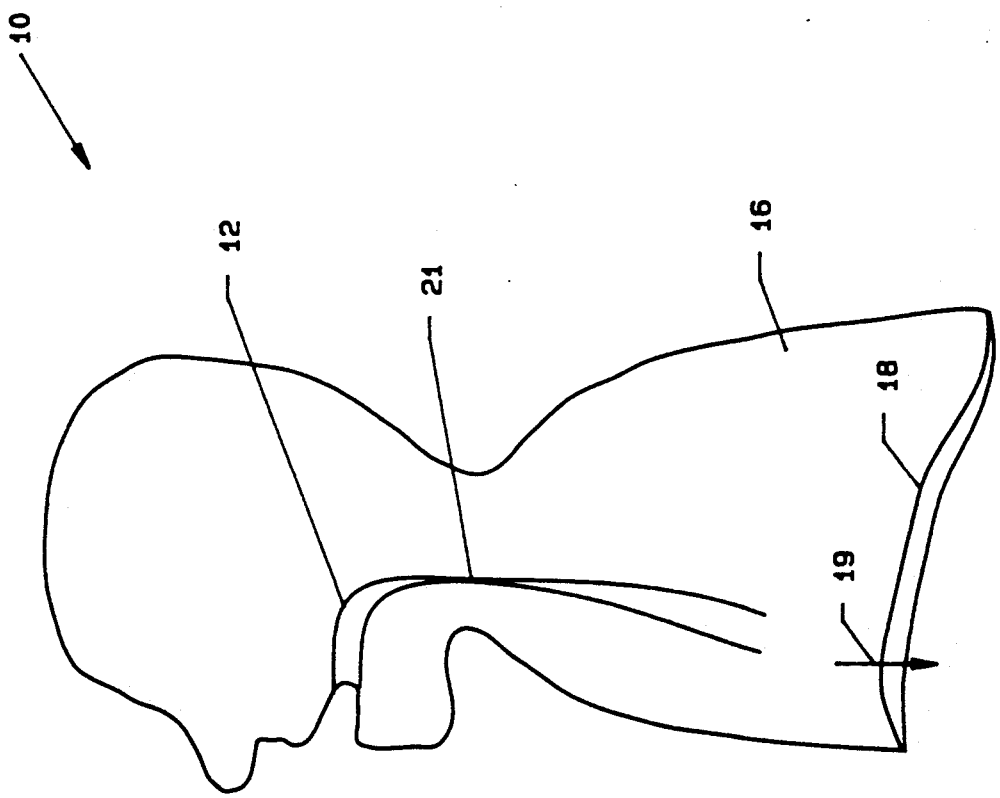
FIG. 2 is a schematic diagram of the respiratory system of a patient during an obstructive sleep apnea event.

FIG. 2 is a schematic diagram of the respiratory system of patient 10 during an obstructive apnea event. During inspiration, upper airway 12 tends to collapse producing an obstruction to air flow at point 21. The above referenced literature describes in detail the physiological processes associated with the collapse of upper airway 1.

Figure 3:
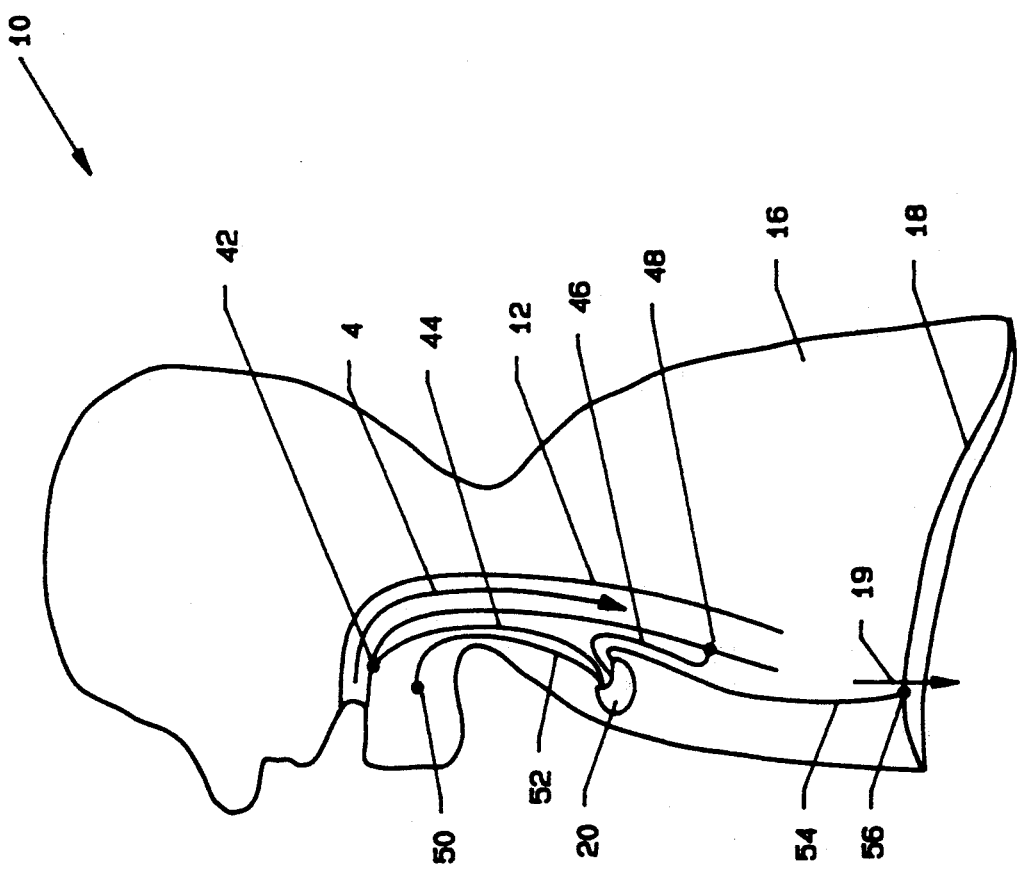
FIG. 3 is a schematic diagram of the respiratory system of a patient having a stimulation system according to the present invention.

FIG. 3 is a schematic diagram of patient 10 showing implantation of an electrical stimulation system for the treatment of obstructive sleep apnea. Implantable pulse generator 20 is placed subcutaneously at a convenient position. Diaphragm 18 is electrically monitored via electrode 56 coupled to lead 54 to determine the occurrence of inspiration.

Patency of upper airway 12 during inspiration is monitored by pressure sensor 42 and pressure sensor 48 coupled to implantable pulse generator 20 via cables 44 and 46, respectively. Stimulation of the musculature of upper airway 12 is accomplished via lead 52 coupled to electrode 50. All other referenced elements are as previously described.

Figure 4:
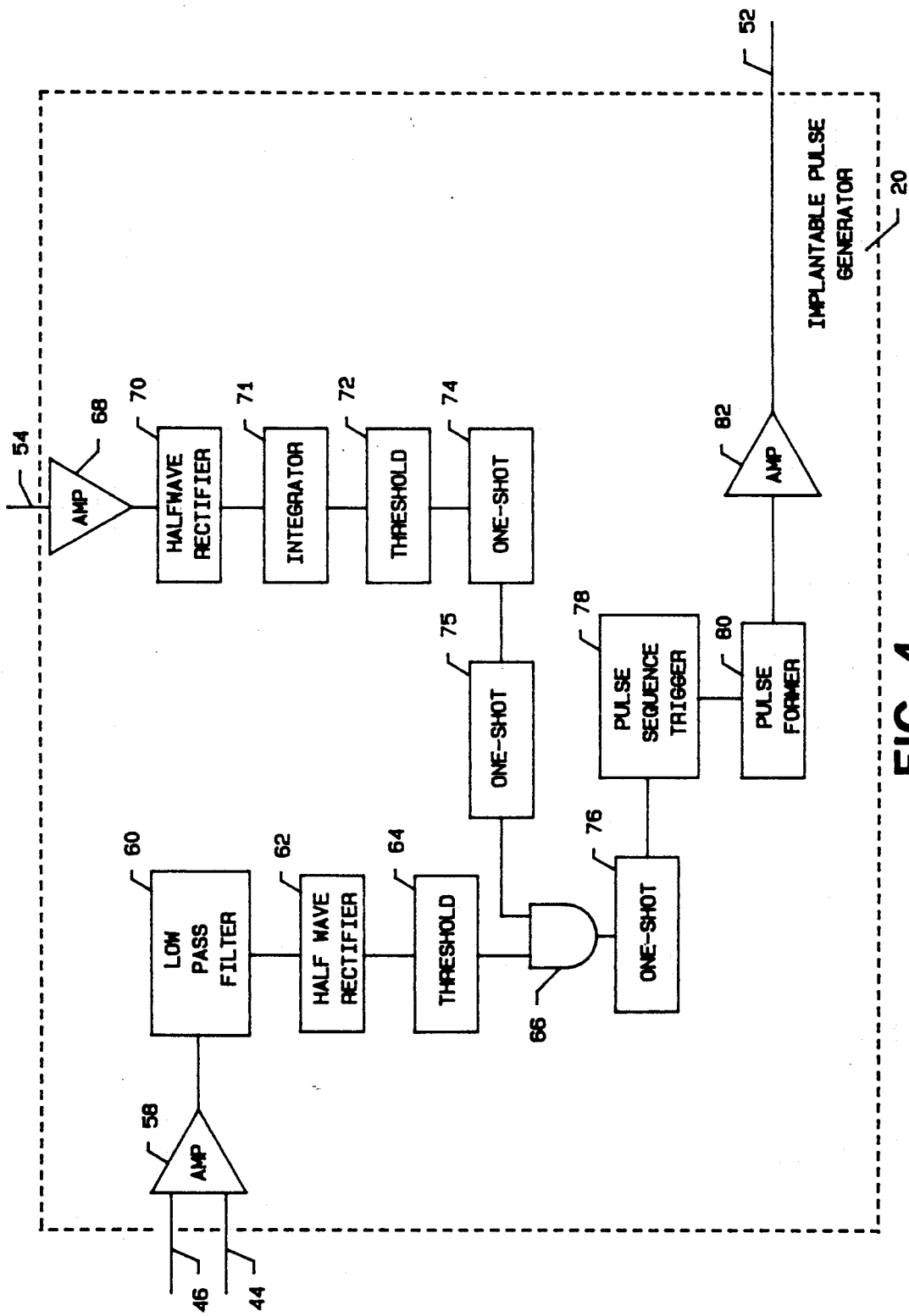
FIG. 4 is a block diagram of an implantable pulse generator.

FIG. 4 is a block diagram showing the operation of implantable pulse generator 20. Pressure sensors 42 and 48 are coupled to sense amplifier 58 via cables 44 and 46, respectively. Sense amplifier 58 functions as a differential amplifier to determine the pressure difference between the location of pressure sensor 42 and the location of pressure sensor 48.

The amplified difference is supplied to low pass filter 60 to remove the high frequency components. The signal is converted to a positive only signal by half wave rectifier 62. This signal is compared to a predetermined level by threshold device 64. Whenever the processed difference in pressure exceeds this predetermined threshold, an obstruction is assumed and threshold 64 provides an output to gate 66.

Electrode 56 is coupled to sense amplifier 68 by lead 54. The signal monitored in this way is the EMG from diaphragm 18 of patient 10 (see also FIG. 3). This bipolar high frequency signal is processed by half wave rectifier 70 and integrator 71 to produce a low frequency positive going indication of inspiration. This processed signal is presented to threshold device 72. Whenever the signal exceeds a predetermined amplitude, inspiration is assumed and an output is provided to one-shot 74. The trailing edge of the output of one-shot 74 triggers one-shot 75 which further delays the signal and provides a uniform electrical response to inspiration.

One-shot 75 provides an output to and gate 66 during the assumed duration of inspiration. And gate 66 provides an output whenever an obstruction is detected during inspiration. This output causes one-shot 76 to supply an output of sufficient duration to enable the stimulation signal during the obstructive apnea event, even though initiation of the stimulation is most likely to cause removal of the obstruction.

When triggered by one-shot 76, pulse sequence trigger 78 provides a pulse train which is of a proper duration and frequency to stimulate the muscles of the upper airway. Pulse former 80 ensures that each of the pulses is of the appropriate pulse width. Output amplifier 82 supplies the pulse train at the desired output amplitude to lead 52 for transfer to electrode 50.

Figure 5:
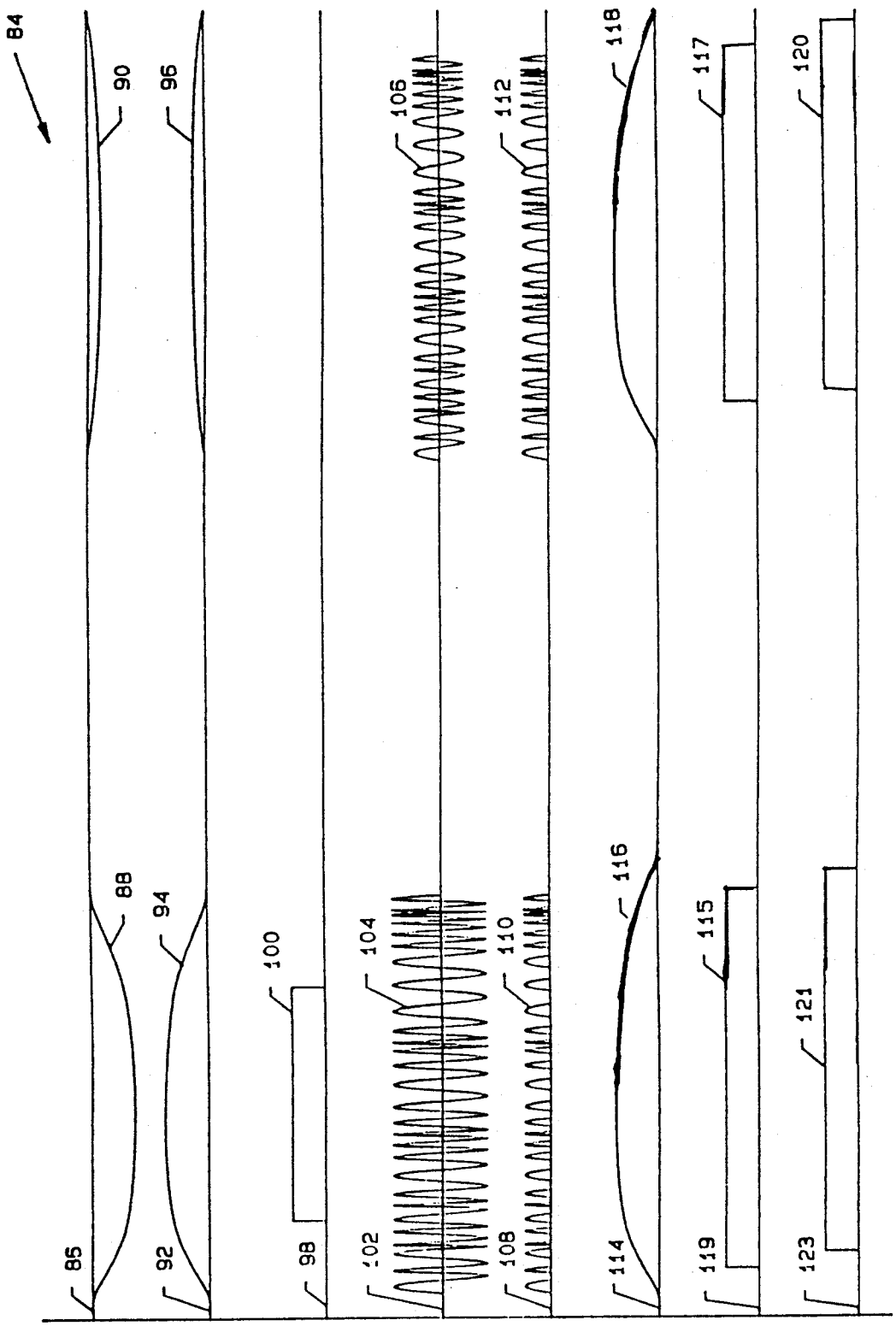
FIG. 5 and 6 are graphical representations of the key signals of the implantable pulse generator.
Figure 6:
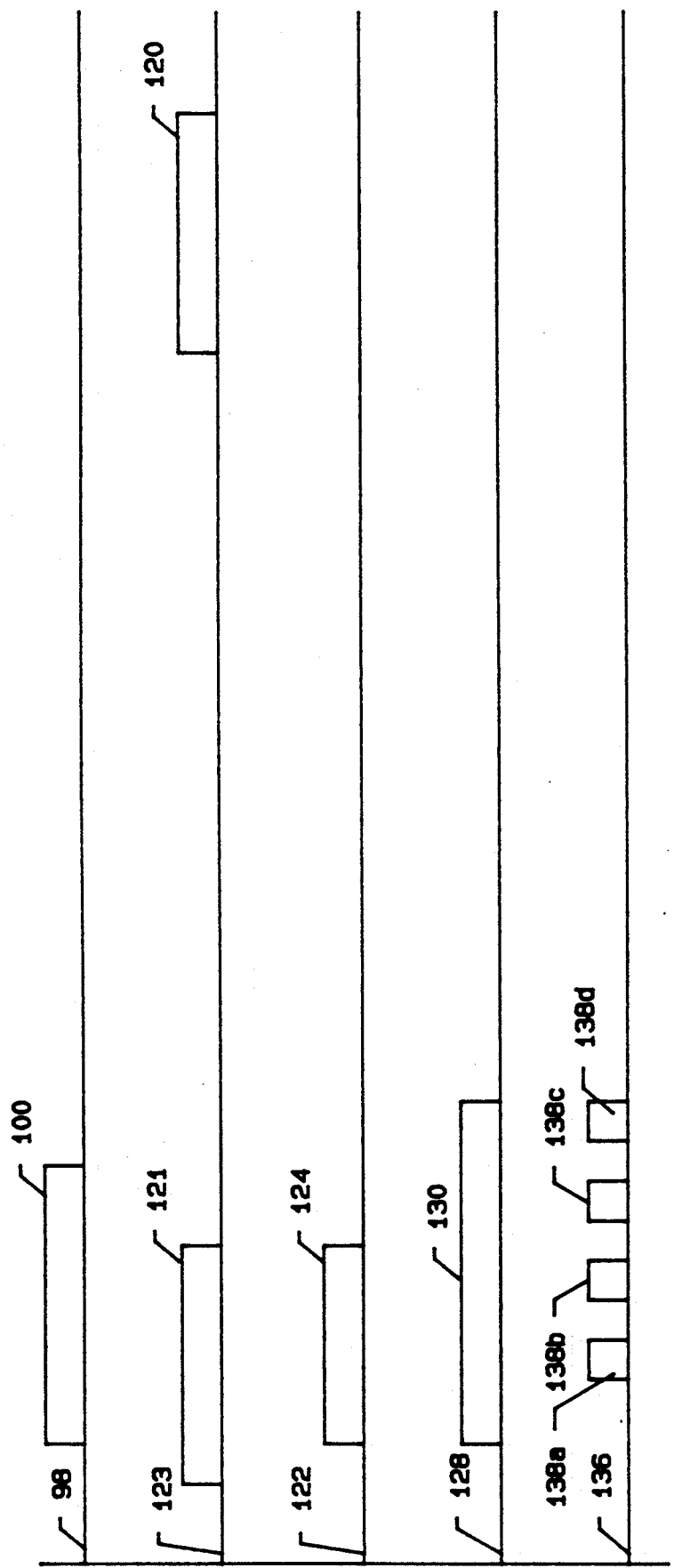

FIGS. 5 and 6 provide a graphical representation 84 of a number of the key signals of implantable pulse generator 20. Line 86 shows the output of sense amplifier 58 of portions of two respiration cycles. Curve 88 represents the output for a relatively large pressure differential between the thorax and the upper airway (see also FIG. 3) as a result of an obstructive apnea event. Curve 90 shows a relatively lesser pressure differential indicating normal upper airway patency.

Line 92 shows the output of half wave rectifier 62 after the signal has been filtered, inverted, and rectified. Again, curve 94 is indicative of an apnea event, and curve 96 is indicative of normal patency. Line 98 shows the output of threshold device 64. Pulse 100 indicates that curve 94 is above the predetermined threshold. Note that curve 96 is not. Pulse 100 is applied to and gate 66 to indicate that an apnea event has been detected (see also FIG. 4).

The EMG sensed by electrode 56 is conducted to sense amplifier 68 by lead 54. Line 102 represents the output of sense amplifier 68. Curves 104 and 106 show the electrical activity associated with contraction of diaphragm 18 (see also FIG. 3). Line 108, containing curves 110 and 112, shows the EMG signal after rectification by half wave rectifier 70. The resultant signal is filtered by integrator 71 to produce curves 116 and 118 on line 114. Note that both curve 116 and curve 118 reach the predetermined threshold of threshold device 72 resulting in pulses 115 and 117 on line 119.

Pulses 115 and 117 represent the times during which inspiration activity is in progress. These signals are delayed by one-shot 75 to provide pulses 121 and 120 and line 123. This delay is necessary because the stimulation and monitoring activities are interactive in the actual system.

FIG. 6 provides a graphical representation of various signals of implantable pulse generator 20. Lines 98 and 123 are presented as the two inputs of and gate 66 (see also FIG. 4). Line 122 represents the output of and gate 66 which is pulse 124 indicating the presence of an obstructive apnea event (i.e. pulse 100) and the occurrence of inspiration (i.e. pulse 121). Note that inspiration associated with pulse 120 produces no output of and gate 66, because line 98 indicates no corresponding obstructive apnea event.

Line 128 represents the output of one-shot 76. Pulse 130 is of a predetermined width to provide the desired length of output pulse train. Line 136 containing individual pulses 138a, 138b, 138c, and 138d are the actual stimulation pulses transferred from output amplifier 82 to stimulation electrode 50 via lead 52.

Having thus described the preferred embodiments of the present invention, those of skill in the art will be readily able to apply the teachings found herein to yet other embodiments within the scope of the claims hereto attached.

We claim:

1. An apparatus comprising:
   a. first means for detecting inspiration;
   b. second means for detecting an obstructive apnea event; and,
   c. means responsively coupled to said first detecting means and said second detecting means for generating a signal to stimulate muscles of an upper airway whenever said first detecting means detects inspiration and said second detecting means detects an obstructive apnea event.

2. An apparatus according to claim 1 wherein said generating means comprises an implantable pulse generator.

3. An apparatus according to claim 2 wherein said signal comprises a pulse train.

4. An apparatus according to claim 3 wherein said first detecting means further comprises an electrode for monitoring EMG.

5. An apparatus according to claim 4 wherein said second detecting means further comprises a pressure sensor.

* * * * *